United States Patent
Kirchner

(10) Patent No.: US 7,320,699 B2
(45) Date of Patent: Jan. 22, 2008

(54) LIGATURE DEVICE FOR BODY PARTS

(75) Inventor: Claudia Kirchner, Markgröningen (DE)

(73) Assignee: Kimetec GmbH, Ditzingen (DE)

( * ) Notice: Subject to any disclaimer, the term of this patent is extended or adjusted under 35 U.S.C. 154(b) by 598 days.

(21) Appl. No.: 10/474,552

(22) PCT Filed: Dec. 5, 2002

(86) PCT No.: PCT/EP02/13773

§ 371 (c)(1),
(2), (4) Date: Oct. 10, 2003

(87) PCT Pub. No.: WO03/051207

PCT Pub. Date: Jun. 26, 2003

(65) Prior Publication Data

US 2004/0127938 A1    Jul. 1, 2004

(30) Foreign Application Priority Data

Dec. 15, 2001    (DE) .............................. 101 61 749

(51) Int. Cl.
*A61B 17/132* (2006.01)
(52) U.S. Cl. ............................ 606/203; 24/614; 24/170
(58) Field of Classification Search ................ 606/201, 606/204, 203, 157; 600/499; 24/311, 635, 24/614–616, 170, 191
See application file for complete search history.

(56) References Cited

U.S. PATENT DOCUMENTS 4,102,343 A * 7/1978 Schneider .................. 606/203
4,561,437 A * 12/1985 Kirchner .................... 606/203
5,084,062 A * 1/1992 Sturm ........................ 606/203
5,314,437 A * 5/1994 Holtsch ..................... 606/157
5,535,485 A * 7/1996 Kirchner .................... 24/170
6,217,601 B1 * 4/2001 Chao ......................... 606/203

FOREIGN PATENT DOCUMENTS

| DE | 42 10 255 C1 | 4/1993 |
| DE | 94 18 598.0 | 1/1995 |
| DE | 296 02 462 U1 | 5/1996 |
| WO | 88/00456 | 1/1988 |

* cited by examiner

*Primary Examiner*—Anhtuan T. Nguyen
*Assistant Examiner*—Elizabeth Houston
(74) *Attorney, Agent, or Firm*—Pauley Peterson & Erickson

(57) ABSTRACT

A ligature device for body parts, with a closure housing, having a base wall, two lateral walls, a cover wall on the upper side thereof and a ligature strap, which may be coupled or is detachably coupled at one end of the closure housing, by a clipping buckle which may be introduced from the rear between an intermediate wall and the cover wall. The above is run or may be run with the other free end thereof between a rocker, pivotably mounted on the base wall and an intermediate wall, arranged at a separation above, through the closure housing, to form a loop and may be clamped by the rocker against a front section of the intermediate wall, connected to the closure housing. Easy manipulation is achieved with a simple construction, whereby the intermediate wall includes a sprung section, projecting from the upper side, by which the rear section of the clipping buckle is raised and pressed, in the assembled state, with the back upper face thereof against a counter support, fixed to the housing. The clipping buckle is held back, against being pulled out, by a rearward retaining element and/or a front retaining element co-operating with a counter element or counter piece of the closure housing and may be released by pressing down on the rear region.

15 Claims, 5 Drawing Sheets

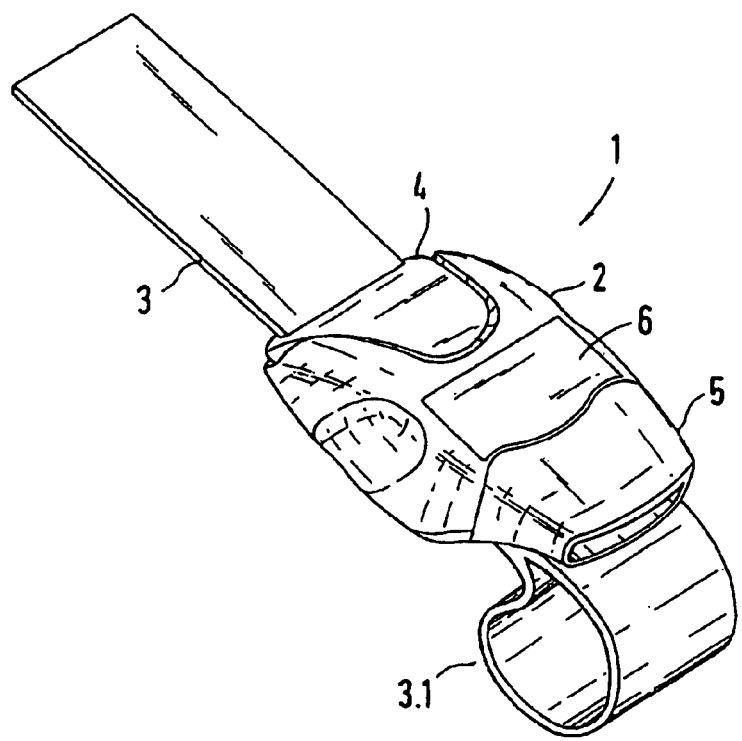
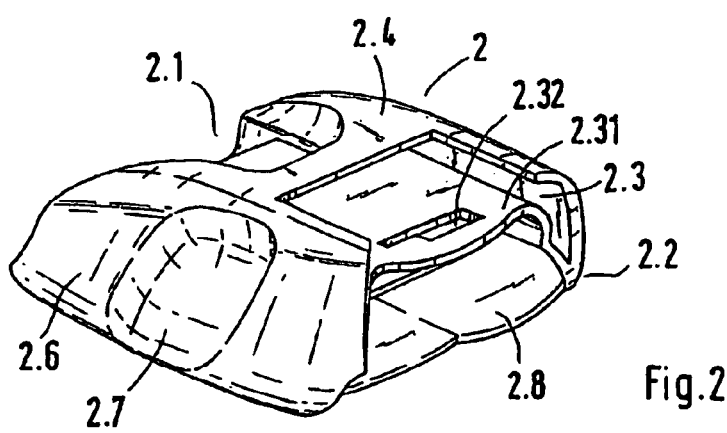

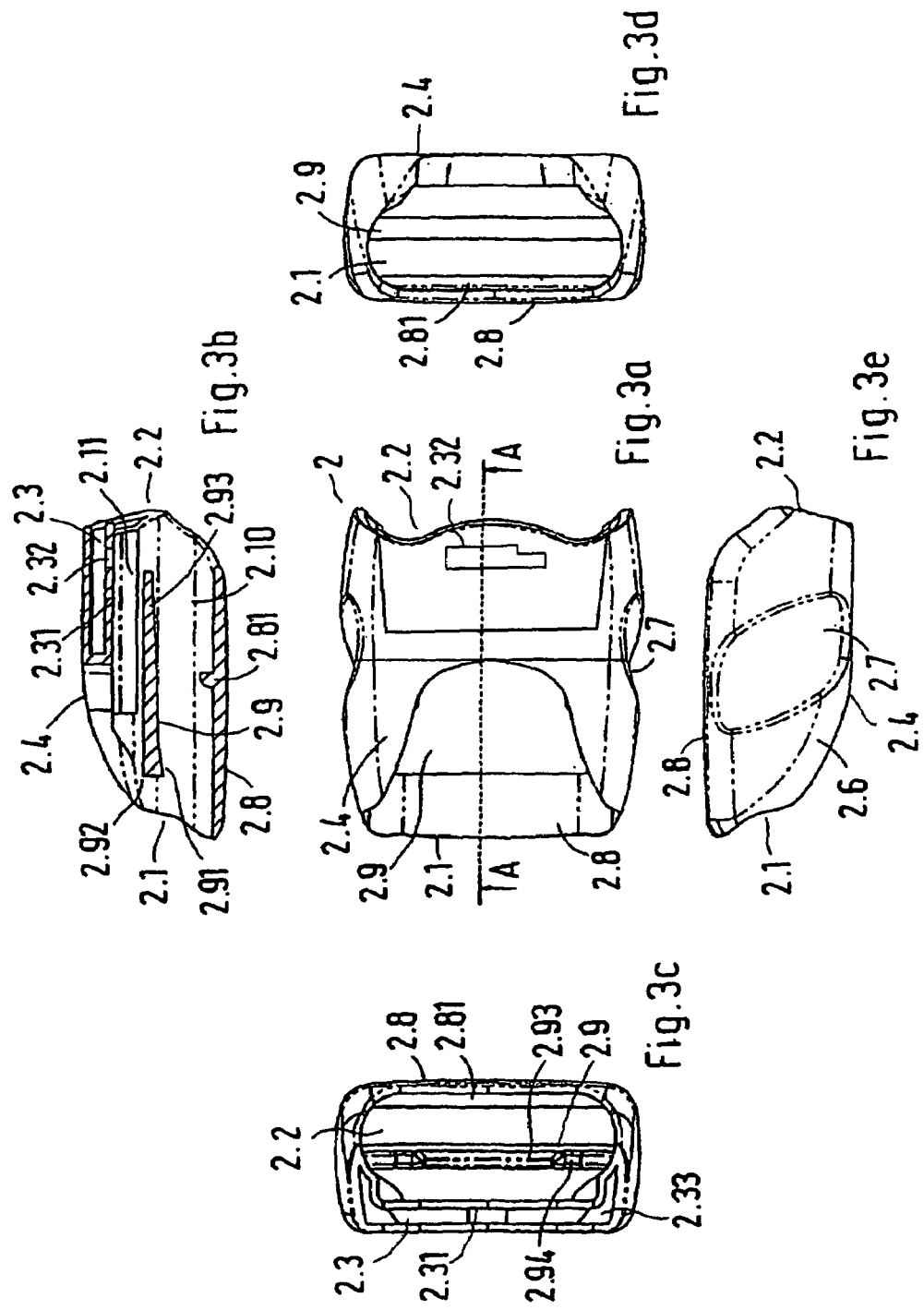

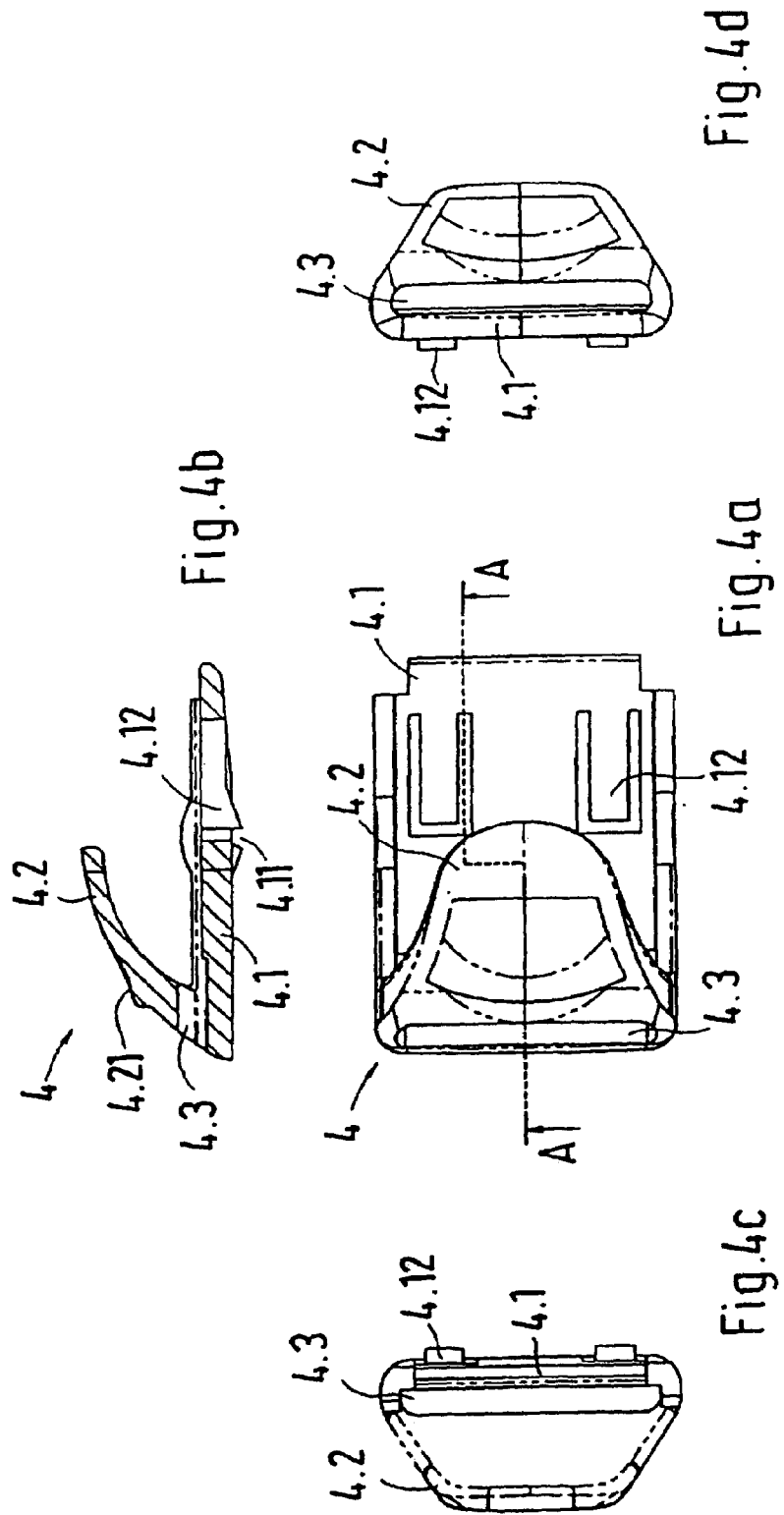

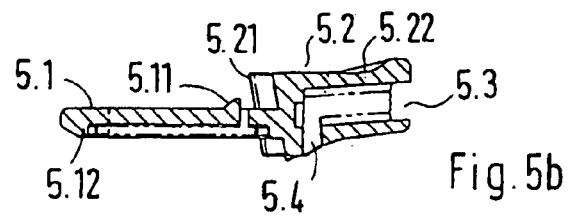
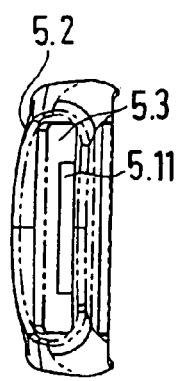
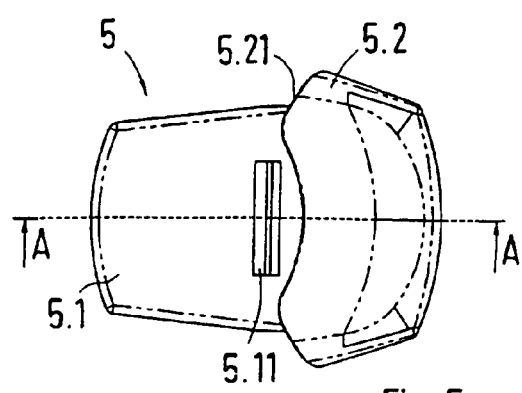
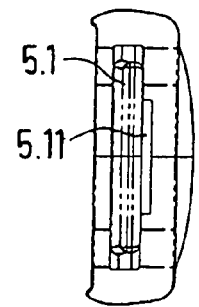
Fig.5b
Fig.5c    Fig.5a    Fig.5d
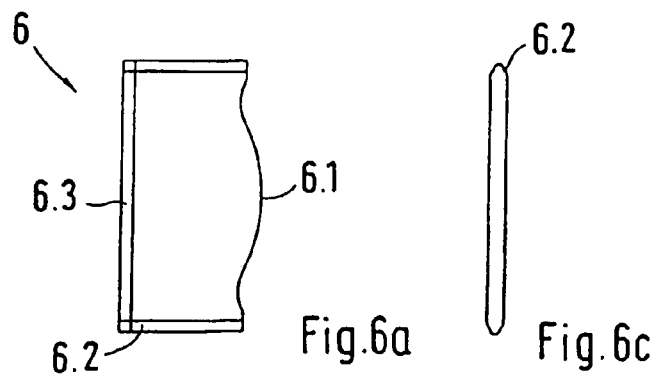
Fig.6b
Fig.6a    Fig.6c

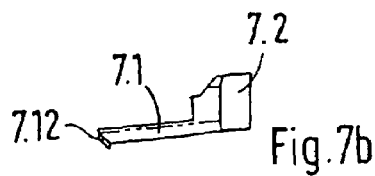
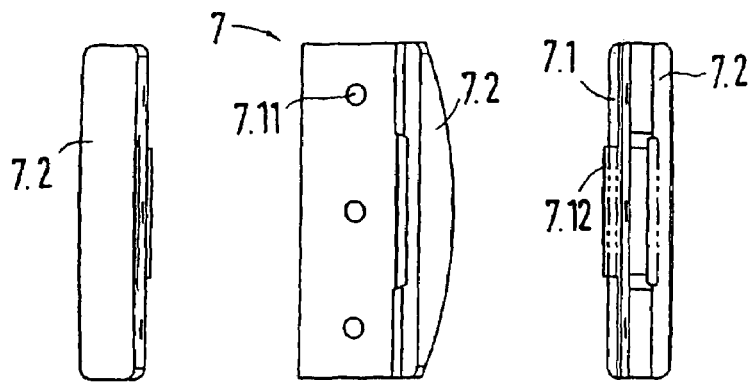
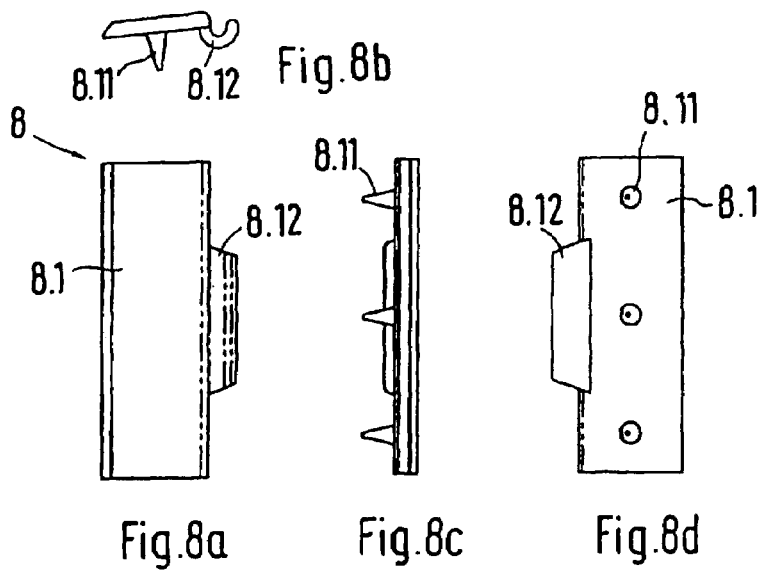

LIGATURE DEVICE FOR BODY PARTS

BACKGROUND OF THE INVENTION

1. Field of the Invention

This invention relates to a tourniquet device for parts of the body, with a closure housing having a bottom wall, two lateral walls and a covering wall on its top, with a tourniquet strap, which is or can be releasably connected with a locking shoe, which can be inserted from a rear between an intermediate wall and the top at the end of the closure housing, which strap is or can be fed with its other free end between a rocker, pivotably seated on the bottom wall, and an intermediate wall arranged at a distance from the bottom wall, through the closure housing and can be clamped by the rocker against a front section of the intermediate wall, which is connected with the closure housing.

2. Discussion of Related Art

A tourniquet device is taught by German Patent References DE 42 10 255 C1 and DE 94 18 598 U1. A rocker, which transitions on its front into a convex actuating section extending upward and toward the rear, is pivotably seated above a bottom wall of the closure housing and has a pass-through opening in a transition area for passing through a tourniquet strap, which extends above the rocker and which, on the rear of the closure housing, forms a loop, which can be placed around the body part to which the tourniquet is to be applied and is introduced by a locking shoe into a receiving shaft on the rear of the housing and is snapped in place. The tourniquet strap is pushed against the underside of an intermediate wall arranged between the bottom wall and the top and is clamped in place when the rear section of the rocker is pulled downward toward the bottom when applying the tourniquet. The locking shoe has a locking tongue, which projects upward and is supported on the underside of the covering wall and can be pushed downward for unlocking and pulling out the locking shoe with the respective tourniquet strap end by a separate pressure element arranged above the tongue.

SUMMARY OF THE INVENTION

One object of this invention is to provide a tourniquet device of the type mentioned above but which offers advantages regarding its construction and handling.

This object is attained with an intermediate wall that has a resilient section projecting toward the top, by which the rear area of the locking shoe is lifted and, in the introduced state, is pushed with a rear top area against an abutment fixed on the housing. The locking shoe is secured against being pulled out toward the rear by a rear securing element and/or a front securing element, which cooperate with a counter-element or counterpiece of the closure housing, and can be released by pressing its rear area downward.

Because of the steps in accordance with this invention, no separate pressure element is required and a precisely shaped tongue required for dependable functioning in the locking shoe embodied as a movable part can be omitted in particular, and extremely simple handling is achieved.

If the locking shoe has a plug-in section for being plugged into the closure housing, and if an actuating section is connected to its rear for release, the locking shoe can be plugged in and released in a simple manner, for a simple construction. Only two movably seated actuating elements are required for controlling the loop via the rocker, and the complete opening of the loop via the locking shoe.

Operation is easier because the actuating section has a triggering depression on its top, and a fastening receiver for fixing the tourniquet strap is formed in it, so that the operator can concentrate completely on his actual work.

In one embodiment, with the construction the front section of the intermediate wall is formed on both sides on the inside of the adjoining lateral walls, while the rear section is separated by respective gaps from the adjoining lateral walls, or from strips of the intermediate wall formed thereon.

Furthermore, steps are advantageous for achieving dependable locking, wherein on the underside of its front section, the locking shoe has a downwardly projecting securing lug or a depression with a securing shoulder forming the securing element, wherein the securing lug on the underside cooperates with a securing edge, or the depression with a securing projection on the top of the front section of the intermediate wall.

For dependable locking, the rear securing element on the top of the locking shoe can be embodied as an upwardly projecting securing lug or as a depression, wherein the securing lug on the top or the depression cooperate with a counter-element having a support section.

Also, the dependable functioning of the tourniquet device is enhanced because the intermediate wall for clamping the tourniquet strap in place with the rocker has a downwardly projecting acute-angled securing edge as the clamping structure on the front edge of its underside, which is placed to prevent the tourniquet strap from being pulled back.

Functioning and handling, as well as a simple construction, are favored because while leaving open a pass-through opening for the tourniquet strap, a rearward extending and convexly upward curved actuating section is formed on the front of the rocker and has on its top an actuating depression, which is concave toward the top.

In a further advantageous step, a cutout with an insertion element, which is releasably received therein, is provided on the top or covering wall.

In this connection an embodiment which is advantageous with regard to the construction and handling includes the cutout having lateral guide grooves, open toward the rear, into which the insertion element can be pushed. In the inserted state the contour of the rear edge of the insertion element ends flush with contour of the rear edge of the covering wall of the closure housing. The contour of the front of the actuation section is matched to the contour of the rear edge of the insertion element and of the covering wall.

BRIEF DESCRIPTION OF THE DRAWINGS

This invention is explained in greater detail in view of an exemplary embodiment, making reference to the drawings wherein:

FIG. 1 is a perspective plan view of a tourniquet device;

FIG. 2 is a perspective plan view of a closure housing of the tourniquet device shown in FIG. 1;

FIGS. 3a to 3e show various views of the closure housing in accordance with FIG. 2;

FIGS. 4a to 4d show various views of a rocker of the tourniquet device in accordance with FIG. 1;

FIGS. 5a to 5d show various views of a locking shoe of a tourniquet device in accordance with FIG. 1;

FIGS. 6a to 6c show various views of an insertion element in a tourniquet device in accordance with FIG. 1;

FIGS. 7a to 7d show various views of a fixating device for a tourniquet device; and FIGS. 8a to 8d show various views of a counter element for fixing the tourniquet element in place on a locking shoe in accordance with FIG. 5, by a fixating device in accordance with FIG. 7.

DESCRIPTION OF PREFERRED EMBODIMENTS

As its essential components, a tourniquet device 1 shown in FIG. 1 has a closure housing 2, a tourniquet strap 3, which is releasably fixed in place by a locking shoe 5 on the rear of the closure housing 2 and forms a loop 3.1, as well as a rocker 4 arranged in the closure housing 2 for the adjustable clamping of the tourniquet strip 3 in the closure housing 2. As shown in connection with FIG. 2, an insertion element 6, for example in the form of an information plaque, is inserted into an appropriately embodied recess 2.3 on the top of a covering wall 2.4.

The closure housing 2, represented in greater detail in FIG. 2, is enclosed by two lateral walls 2.6 with respective recessed grips 2.7, a bottom wall 2.8 and a covering wall 2.4, and has on its rear an insertion opening for the tourniquet strap 3, and also the locking shoe 5, as well as the insertion element 6. On its front, the closure housing 2 has an outlet opening 2.1, into which the rocker 4 is inserted and from which the tourniquet strap 3 extends with its one end. On its underside, the recess 2.3 is delimited by a wall section 2.31, in which a securing section 2.32, embodied as a rectangular window, is provided, and has lateral guide grooves for pushing the insertion element 6 in from the rear 2.2, wherein the guide grooves are formed between the wall section 2.31 and sections of the covering wall 2.4 on both sides, as well as the sections of the lateral walls 2.6 which form the groove bottom. The recess 2.3 can also be embodied in a groove-like manner in a front area in order to receive a front edge 6.3 of the insertion element 6, as shown in FIG. 6, in its completely pushed-in state.

As shown in greater detail in the plan views of FIG. 3, in particular the representations in FIGS. 3b, 3c and 3d, an intermediate wall 2.9 is attached inside the closure housing 2 between the covering wall 2.4 and the bottom wall 2.8 and is preferably formed on the latter, by which a pass-through shaft 2.10 for the tourniquet strap 3 is formed between the bottom wall 2.8 and the underside of the intermediate wall 2.9. Also, a receiving shaft 2.11 for inserting a plug-in section 5.1 of the locking shoe 5 (see FIG. 5) is formed between the top of the intermediate wall 2.9 and the underside of the covering wall 2.4, or of the wall section 2.31 formed on it. On its underside the intermediate wall 2.9 has a securing structure for clamping the tourniquet strap 3 in place, and its front lower edge 2.91 in particular is embodied at an acute angle, which results in a certain amount of resistance opposite the pulling direction of the tourniquet strap 3 when it is operating. The front upper edge forms a securing edge 2.92 in the form of a securing lug for a hook-shaped securing element 5.12 on the underside of the plug-in section 5.1 of the locking shoe 5. As shown in FIG. 3c, a resilient section 2.93 is formed in the rear section of the intermediate wall 2.1, which can extend forward past the center, by lateral notches, or gaps 2.94 opposite lateral sections of the intermediate wall 2.9 connected with the lateral walls 2.6. In the front area the intermediate wall 2.9 is continuously connected with the lateral walls 2.6, it is formed on them in particular.

A rib-like pivot support 2.81 is formed on the top of the bottom wall 2.8 of the closure housing 2 as a pivot bearing and for securing the rocker 4, which can also be seen in FIGS. 3b, 3c and 3d.

Details of the rocker 4 are represented in FIGS. 4a to 4d. The rocker plate 4.1, which is pivotably seated by a pivot bearing 4.11 between transversely extending ribs or nubs on the pivot support 2.81, makes a transition in its front end area into an actuating section 4.2, which is convex toward the front and upward and has a triggering depression 4.21 approximately in its center area, which is concave toward the top and has a beaded front edge for simpler tactile recognition and operation. A pass-through opening 4.3 for the tourniquet strap 3 is formed in the transition area between the rocker plate 4.1 and the actuating section 4.2. On the underside of the rocker plate 4.1, the pivot bearing 4.11 is restricted at its rear by downward extending spring tongues 4.12 with an insertion slope, so that the rocker 4 can be easily inserted from the front, guided in lateral grooves or similar guide tracks, into the pass-through shaft 2.10 of the closure housing 2 and snapped into the pivot support 2.81, and can also be released again by the spring tongues 4.12. In a top view, the actuating section 4.2 has the shape of a tongue and is, tapering toward the top, in the shape of a continuous curvature and fitted into a correspondingly shaped recess in the covering wall 2.4 of the closure housing 2.

The locking shoe 5, shown in greater detail in FIGS. 5a to 5d, has in its rear area an actuating section 5.2, which is formed on the plug-in section 5.1, projects to the rear beyond the closure housing 2 in the inserted state and has an upwardly concave triggering depression 5.22 on its top. In a top view, the front edge of the actuating section 5.2 is symmetrically curved and has two curvature sections, which make a steady transition into each other via a central curved section and are laterally convex toward the front and matched to a correspondingly extending contour of the rear edge of the covering wall 2.4 of the closure housing 2, so that definite seating results in the inserted state. In the interior, the actuating section 5.2 has a fixation receiver 5.3, open toward the rear, for receiving a fixating element 7 with a counter-element 8 (see FIGS. 7 and 8) for fixing the tourniquet strap 3 in place, wherein the tourniquet strap 3 is extended out of an outlet opening 5.4 on the underside of the actuating section 5.2. The plug-in section 5.1 which is formed on the actuating section 5.2 and adjoins it at the front, has in its rear edge area an upward projecting securing element 5.11, with which the locking shoe 5 is supported in the inserted state against the rear edge of the securing section 2.32 in the wall section 2.31 of the closure housing 2, wherein the locking shoe 5 is pushed upward by the rear resiliently acting section of the intermediate wall 2.9. In addition, on the underside of the front section of the plug-in section 5.1, the securing element 5.12 is hooked to the front securing edge 2.92 of the intermediate wall 2.9. For releasing the locking shoe 5 it is only necessary to press it downward by pushing on the actuating section 5.2, so that the securing element 5.11 on the one hand, and the securing element 5.12 on the other hand are released and the locking shoe 5 is disengaged and is automatically pulled at least partially by the pull of the preferably elastic tourniquet strap 3 out of the receiving shaft 2.11 and can then be taken out completely for opening the loop 3.1.

The insertion element 6, shown in greater detail in FIG. 6, preferably has lateral edges 6.2, which are conical in cross section, and a rear edge 6.2, which extends complementarily to the front edge of the actuating section 5.2 of the locking shoe. The element is held by a defined clamping effect, but can be manually pushed out, in the recess 2.3. For identification the inserting element 6 can be designed in a desired color, or can be transparent for placing information underneath it, for example a name plate, or can have a suitable legend.

The fixating device represented in FIGS. 7a to 7d has a fixation plate 7.1 with fixating elements 7.11 in the form of openings, and a hook element 7.12, which projects downward from its front, and on its rear makes a transition into a fixation block 7.2 formed on it. For fixing the tourniquet strap 3 in place, its end area is placed on the top of the fixation plate 7.1, is covered by a counter-plate 8.1 by the counter-element 8 shown in FIG. 8 and is fixed in place by counter-elements 8.11 in the shape of spike-like pins matched to the openings 7.11, after which the fixating element 7 and the counter-element 8 are clamped into the fixation receiver 5.3 of the locking shoe 5 and are held therein by the hook element 7.12, wherein the counter-plate 8.1 is supported by a support member 8.12 in the fixation receiver 5.3 with respect to the hook element 7.12 which engages the outlet opening 5.4.

A simple operation, along with a simple construction and good functioning, results from the described measures.

The invention claimed is:

1. A tourniquet device (1) for parts of a body, with a closure housing (2) having a bottom wall (2.8), two lateral walls (2.6) and a covering wall (2.4) on a top, a tourniquet strap (3) releasably connected with a locking shoe (5) and an end of the tourniquet strap (3) at the closure housing (2) which is insertable from a rear of the closure housing (2) between an intermediate wall (2.9) and the bottom wall (2.8), the strap insertable with a free end between a rocker (4), pivotably seated on the bottom wall (2.8), and the intermediate wall (2.9) arranged at a distance from the bottom wall (2.8), through the closure housing (2) and clampable by the rocker (4) against a front section of the intermediate wall (2.9), which is connected with the closure housing (2), the tourniquet device (1) comprising:

the intermediate wall (2.9) having a resilient section (2.93) projecting toward the covering wall (2.4) by which a rear area of the locking shoe (5) is lifted and in an introduced state is pushed with a rear top area against a wall section (2.31) fixed on the housing, the front section of the intermediate wall (2.9) connected on both sides to an inside of the lateral walls (2.6), and the resilient section (2.93) formed in a rear section of the intermediate wall (2.9) between two gaps (2.94) which separate the resilient section from the lateral walls (2.6), wherein the locking shoe (5) is secured against being pulled out toward the rear by at least one of a rear securing element (5.11) and a front securing element (5.12), which cooperate with one of a counter-element (2.32) and a counterpiece (2.92) of the closure housing (5), and is releasable by pressing the rear area of the locking shoe (5) downward.

2. The tourniquet device in accordance with claim 1, wherein the locking shoe (5) has a plug-in section (5.1) for plugging into the closure housing (2), and for releasing has an actuating section (5.2) connected to the rear.

3. The tourniquet device in accordance with claim 2, wherein the actuating section (5.2) has a triggering depression (5.22) on the top, and a fastening receiver (5.3) for fixing the tourniquet strap (3) in place is formed in the actuating section (5.2).

4. The tourniquet device in accordance with claim 3, wherein on an underside of a front section the locking shoe (5) has one of a downwardly projecting securing lug and a depression with a securing shoulder forming the securing element, wherein one of the securing element on an underside cooperates with one of a securing edge (2.92) and the depression with a securing projection on the top of the front section of the intermediate wall.

5. The tourniquet device in accordance with claim 4, wherein a rear securing element (5.11) on the top of the locking shoe (5) is one of an upwardly projecting securing lug and a depression that cooperates with a counter-element having a support section.

6. The tourniquet device in accordance with claim 5, wherein the intermediate wall (2.9) for clamping the tourniquet strap in place by the rocker (4) has a downwardly projecting acute-angled securing edge as the clamping structure (2.91) on a front edge of the underside which prevents the tourniquet strap (3) from being pulled back.

7. The tourniquet device in accordance with claim 6, wherein with an open pass-through opening (4.3) for the tourniquet strap (3), a rearward extending and convexly upward curved actuating section (4.2) is formed on the front or the rocker (4) and has on a top an actuating depression (4.21) which is concave toward the top.

8. The tourniquet device in accordance with claim 7, wherein a cutout (2.3) with an insertion element (6) releasably received therein, is provided on the covering wall (2.4).

9. The tourniquet device in accordance with claim 8, wherein the cutout (2.3) has lateral guide grooves (2.33) open toward a rear into which the insertion element (6) is pushed, and a contour of a front of the actuation section (5.2) is matched to a second contour of the covering wall (2.4).

10. The tourniquet device in accordance with claim 1, wherein on an underside of a front section the locking shoe (5) has one of a downwardly projecting securing lug and a depression with a securing shoulder forming the securing element, wherein one of the securing element on an underside cooperates with one of a securing edge (2.92) and the depression with a securing projection on the top of the front section of the intermediate wall.

11. The tourniquet device in accordance with claim 1, wherein a rear securing element (5.11) on a top of the locking shoe (5) is one of an upwardly projecting securing lug and a depression that cooperates with a counter-element having a support section.

12. The tourniquet device in accordance with claim 1, wherein the intermediate wall (2.9) for clamping the tourniquet strap in place by the rocker (4) has a downwardly projecting acute-angled securing edge as a clamping structure (2.91) on a front edge of the underside which prevents the tourniquet strap (3) from being pulled back.

13. The tourniquet device in accordance with claim 1, wherein with an open pass-through opening (4.3) for the tourniquet strap (3), a rearward extending and convexly upward curved actuating section (4.2) is formed on the front or the rocker (4) and has on a top an actuating depression (4.21) which is concave toward the top.

14. The tourniquet device in accordance with claim 1, wherein a cutout (2.3) with an insertion element (6) releasably received therein, is provided on the covering wall (2.4).

15. The tourniquet device in accordance with claim 14, wherein the cutout (2.3) has lateral guide grooves (2.33) open toward a rear into which the insertion element (6) is pushed, and a contour of a front of the actuation section (5.2) is matched to a second contour of the covering wall (2.4).

* * * * *